United States Patent
Kawano

(10) Patent No.: US 10,775,345 B2
(45) Date of Patent: Sep. 15, 2020

(54) ANALYTICAL METHOD AND ANALYTICAL SYSTEM

(71) Applicant: ARKRAY, Inc., Kyoto (JP)

(72) Inventor: Masao Kawano, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 272 days.

(21) Appl. No.: 15/793,604

(22) Filed: Oct. 25, 2017

(65) Prior Publication Data

US 2018/0120256 A1    May 3, 2018

(30) Foreign Application Priority Data

Oct. 27, 2016 (JP) .................. 2016/210273
Oct. 20, 2017 (JP) .................. 2017-203648

(51) Int. Cl.
*G01N 27/447*  (2006.01)
*G01N 33/487*  (2006.01)
(Continued)

(52) U.S. Cl.
CPC ....... *G01N 27/44721* (2013.01); *G01N 21/27* (2013.01); *G01N 27/44769* (2013.01);
(Continued)

(58) Field of Classification Search
CPC ............... G01N 27/447; G01N 27/26; G01N 27/44769; G01N 27/44791;
(Continued)

(56) References Cited

U.S. PATENT DOCUMENTS 7,223,325 B2   5/2007 Landers et al.
2010/0155241 A1   6/2010 Ross et al.
(Continued)

FOREIGN PATENT DOCUMENTS

EP   2993467 A1   3/2016
JP   S60-073458 A   4/1985
(Continued)

OTHER PUBLICATIONS

Extended European Search Report issued in corresponding European Patent Application No. 17198692.0 dated Jan. 11, 2018.

*Primary Examiner* — Gurpreet Kaur
(74) *Attorney, Agent, or Firm* — Morgan, Lewis & Bockius LLP

(57) ABSTRACT

An analytical method and an analytical system capable of more accurate analysis, in which a sample is analyzed by a capillary electrophoresis technique in which a voltage is applied to a sample solution introduced to a micro flow path, a separation analysis is performed for a component contained in the sample solution, and an optically measured value corresponding to an elapsed time after starting a measurement is measured. The analytical method comprises: a process of determining an interface arrival time point, based on the optically measured value when an interface between the sample solution and a migration liquid reaches a predetermined measurement position in the micro flow path; and a process of identifying the component contained in the sample solution using the optically measured value at the elapsed time after the interface arrival time point.

15 Claims, 26 Drawing Sheets

(51) Int. Cl.
*G01N 21/27* (2006.01)
*G01N 30/86* (2006.01)

(52) U.S. Cl.
CPC ..... *G01N 27/44791* (2013.01); *G01N 30/861* (2013.01); *G01N 33/48707* (2013.01); *G01N 2030/8648* (2013.01)

(58) Field of Classification Search
CPC ....... G01N 27/44721; G01N 33/48707; G01N 30/8603; G01N 30/861
See application file for complete search history.

(56) References Cited

U.S. PATENT DOCUMENTS

| | | | | |
|---|---|---|---|---|
| 2016/0077053 | A1* | 3/2016 | Onuma | G01N 27/44791 204/453 |
| 2016/0139078 | A1* | 5/2016 | Henry | G01N 27/44765 204/645 |

FOREIGN PATENT DOCUMENTS

| | | |
|---|---|---|
| JP | H11-337521 A | 12/1999 |
| JP | 2016-057289 A | 4/2016 |

* cited by examiner

ANALYTICAL METHOD AND ANALYTICAL SYSTEM

BACKGROUND

Technical Field

The present invention relates to an analytical method and an analytical system.

Related Art

Various types of proteins are analyzed as indicators indicating biometric states. Among them, as to hemoglobin (Hb) in blood cells, there are plural hemoglobin types, i.e., normal hemoglobin (HbA) and other plural types of variant hemoglobins (HbC, HbD, HbE, HbS, etc.).

When analyzing a component analysis of a sample (by, e.g., liquid chromatography, etc.), for example, a control sample of known composition is measured in advance in order to confirm a detection time and a peak profile corresponding to a component of the control sample to be detected, which are compared to an analysis result of the sample to identify the component thereof (cf., e.g., JP S60-73458 A).

In analysis of a hemoglobin type as a component in blood as a sample, difference of a detection time for each component is utilized for separation analysis. In such separation analysis, considering that each measurement may have some variations (e.g., difference of a detection time due to a column deterioration and storage condition of an eluent, etc.), for example, if a detection time of some component falls in a predetermined detection time range, the component is identified to be a particular known component.

A capillary electrophoresis technique is employed as a technique to analyze hemoglobin (Hb) (cf., e.g., JP H11-337521 A). Sample analysis using a capillary electrophoresis technique is performed in a state in which an analysis chip is loaded into an analysis device. The analysis chip retains a sample and provides a place for the target sample to be analyzed. The analysis chip may be a disposable analysis chip intended for disposal after completing only a single analysis. A hemoglobin analytical method using such a disposable analysis chip is described, for example, in JP 2016-57289 A.

A waveform obtained by analysis includes peaks and the like corresponding to specific components. Which peaks correspond to which specific component is identified by considering an elapsed time from a time point serving as a reference for analysis to a time point obtained for the relevant peak and the profile of the relevant peak, etc. Then, identification of a specific component sometimes becomes inaccurate depending on whether or not the time point serving as the reference reflects the start time point of the electrophoresis. In particular, in cases in which a disposable analysis chip is used, there is possibility of an error occurring in the elapsed time from the time point serving as the reference to the time point when the peak of the specific component is obtained, due to lot-to-lot differences in each analysis chip and individual differences within the same lot. In particular, hitherto, the time point when a voltage starts to be applied is generally taken as the time point serving as the reference (t=0). In such cases, for disposable analysis chips, there is an issue of increased error in the elapsed time from the time point t=0 to the time point when the specific component occurs due to individual differences in each analysis chip.

As other related technology to address such an issue, there are methods in which a known waveform is used as the reference. One known waveform identifying method is a method in which a reference liquid having a known waveform is introduced onto the same analysis chip before a sample is introduced, and the measurement waveform thereof is utilized to compute any error caused between individual differences in chips. Based on this computed error information, the method then utilizes waveform determination on a sample introduced while using the same analysis chip. However, there is the issue that the reference liquid needs to be added, which takes time and is also costly. Moreover, this method is inherently not applicable for disposable analysis chips that are disposed of after each measurement.

Further, as other related technology to address such an issue, there is a method that employs a peak value of a component contained in the introduced sample and having a representative and characteristic waveform, or a peak value of a reference substance added to the sample and acting as a typical peak value. However, in cases in which the specific component included in the introduced sample is unknown, sometimes the time point where the peak of the specific component occurs and the waveform are shifted, there is an overlap with other components, or the like, making it difficult to identify the peak of the specific component. In particular, in cases in which the specific component is hemoglobin, for example, as to HbA and HbS types of hemoglobin, their waveforms differ greatly, leading to the issue of sometimes being affected by overlap with the reference component and interaction with the reference substance. Further, methods in which a reference substance is added are difficult to commercialize due to the cost of the reference substance, and the need to consider the impact of its interaction with other components.

SUMMARY

In consideration of the above circumstances, the present invention relates to provide an analytical method and an analytical system capable of more accurate analysis.

An analytical method provided by a first aspect of the present invention is an analytical method for analyzing a sample by a capillary electrophoresis technique in which a voltage is applied to a sample solution introduced to a micro flow path, a separation analysis is performed for a component contained in the sample solution, and an optically measured value corresponding to an elapsed time after starting a measurement is measured. The analytical method includes: a process of determining an interface arrival time point, based on the optically measured value when an interface between the sample solution and a migration liquid reaches a predetermined measurement position in the micro flow path; and a process of identifying the component contained in the sample solution using the optically measured value at the elapsed time after the interface arrival time point.

The "predetermined measurement position in the micro flow path" in the foregoing means a position where a measurement light is transmitted through for measuring the optically measured value. Although the optically measured value in accordance to the interface is preferably measured at the same position where the optically measured value in accordance to the component to be identified, it may be measured at the different position.

Note that in the above analytical method, the sample solution is a solution that contains a subject sample to be analyzed and that the conception of the sample solution contains both a case where the sample occupies 100% of the solution and a case where the sample is diluted properly. The sample solution is not particularly limited, as long as the interface arrival time point can be identified and it is in a state of liquid. The liquid may be a diluted solution in which a solid as the sample is, for example, suspended, dispersed, or dissolved in a liquid medium. In case that the sample is liquid, for example, the undiluted sample may be employed as the sample solution as it is. If the concentration of the sample is too high, the undiluted sample may be diluted by, for example, suspending, dispersing, or dissolving in a liquid medium to be the sample solution to be used. There are no particular limitations to the liquid medium as long as the liquid medium is capable of suspending, dispersing, or dissolving the sample, and examples of the liquid medium include water or a buffer solution. Examples of the sample include, for example, a specimen from a biological body, a specimen taken from the environment, a metal, a chemical substance, a drug, etc. The specimen from a biological body is not particularly limited, and examples thereof include urine, blood, hair, saliva, sweat, nails, etc. The blood specimen may, for example, be erythrocytes, whole blood, serum, blood plasma, etc. Examples of the biological body include a human, a non-human animal, a plant, etc., and the non-human animal may, for example, be a mammal other than a human, a reptile, an amphibian, a fish, an insect, etc. The specimen taken from the environment is not particularly limited, and examples thereof include a food product, water, soil, the atmosphere, an air sample, etc. Examples of the food include, for example, fresh food products, processed food products, etc. Examples of the water include, for example, drinking water, underground water, river water, sea water, household effluent, etc.

In a preferable embodiment of the present invention, the sample solution is a solution containing blood as the sample, and the component is hemoglobin.

In a preferable embodiment of the present invention, the interface arrival time point is determined based on a change in the optically measured value when the interface reaches the predetermined measurement position in the process of determining the interface arrival time point.

In a preferable embodiment of the present invention, the optically measured value is an absorbance of the sample solution, a process of forming a waveform related to the absorbance corresponding to the elapsed time after starting the measurement is performed before the process of determining the interface arrival time point, and the change in the optically measured value in the process of the determining the interface arrival time point is a change occurring in the waveform.

In a preferable embodiment of the present invention, the process of forming the waveform includes a step of forming a differential waveform in which differential values obtained by differentiating the waveform related to the absorbance with respect to time are expressed as a waveform corresponding to the elapsed time, and the differential waveform is used in the process of determining the interface arrival time point.

In a preferable embodiment of the present invention, the process of determining the interface arrival time point includes: a step of determining a reference value established on the basis of the differential waveform within a predetermined search time range; a step of determining a first specific point and a second specific point with reference to a degree of separation from the reference value within the predetermined search time range; a step of specifying an average value point having a position between the first specific point and the second specific point on a time axis, and having a differential value that is an average of differential values of the first specific point and the second specific point; and a step of determining a time point of the average value point as the interface arrival time point.

In a preferable embodiment of the present invention, the step of determining the first specific point and the second specific point includes: a step of taking a point, which is located furthest from the reference value at a negative direction side along a differential value axis within the predetermined search time range, as a first feature point; a step of taking a point, which is located furthest from the first feature point along the differential value axis at a negative direction side along the time axis within the predetermined search time range, as a second feature point; a step of taking a point, which is located furthest from the first feature point along the differential value axis at a the positive direction side along the time axis within the predetermined search time range, as a third feature point; a step of taking a point, which is located furthest from the third feature point at a positive direction side along the time axis within the predetermined search time range, as a fourth feature point; and a step of selecting two points among the first to fourth feature points that are located furthest from each other along the differential value axis as the first specific point and the second specific point.

In a preferable embodiment of the present invention, a disposable analysis chip provided with the micro flow path is used.

An analytical system provided by a second aspect of the present invention is an analytical system for analyzing a sample by using a separation analysis method, in which a voltage is applied to a sample solution introduced to a micro flow path, a separation analysis is performed for a component contained in the sample solution, and an optically measured value corresponding to an elapsed time after starting a measurement is measured. The analytical system comprises a measurement section configured to measure the optically measured value of a liquid in the micro flow path and control section configured to perform analysis processing using a measurement result obtained from the measurement section. The control section comprises: a means for determining an interface arrival time point based on the optically measured value when an interface between the sample solution and a migration liquid reaches a predetermined measurement position in the micro flow path; and a means for identifying the component contained in the sample solution using the optically measured value at the elapsed time after the interface arrival time point.

In a preferable embodiment of the present invention, the sample solution is a solution containing blood as the sample, and the component is hemoglobin.

In a preferable embodiment of the present invention, the interface arrival time point is determined based on a change in the optically measured value when the interface reaches the predetermined measurement position in the means for determining the interface arrival time point.

In a preferable embodiment of the present invention, the optically measured value is an absorbance of the sample solution; the analytical system further comprises a means for forming a waveform related to the absorbance corresponding to the elapsed time after starting the measurement; and the means for determining the interface arrival time point determines the interface arrival time based on a change occurring in the waveform as the change in the optically measured value.

In a preferable embodiment of the present invention, a disposable analysis chip provided with the micro flow path is used.

Advantageous Effects of Invention

An aspect of the present invention enables more accurate analysis.

Other features and advantages of an aspect of the present invention will become apparent from the detailed description that follows, with reference to the attached drawings.

DETAILED DESCRIPTION

Explanation follows regarding specifics of a preferable embodiment of the present invention, with reference to the drawings.

Figure 1:
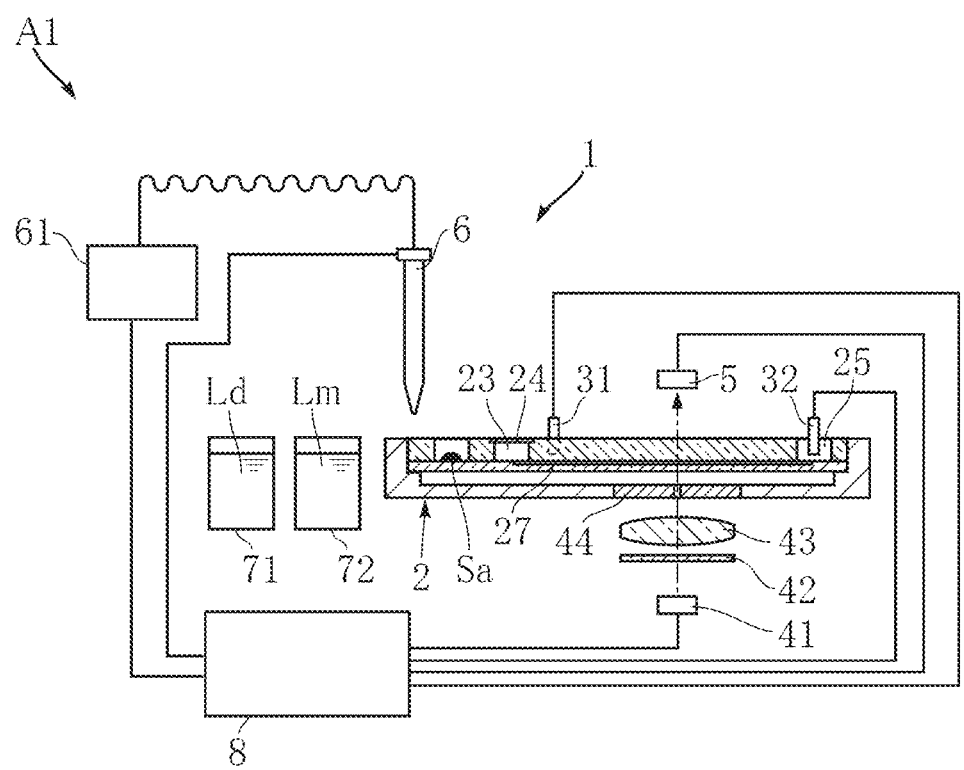
FIG. 1 is a system schematic diagram illustrating an example of an analytical system according to an embodiment of the present invention.

FIG. 1 illustrates schematic configuration of an example of an analytical system according to an embodiment of the present invention. An analytical system A1 is configured including an analysis device 1 and an analysis chip 2. The analytical system A1 is a system that executes an analytical method using a separation analysis method on a sample Sa as an analysis target. The sample Sa is not particularly limited, and in the present embodiment, explanation will be regarding blood collected from a human body as an example of the sample Sa. Of the components contained in the sample Sa, those components which are subject to analysis are defined as being analysis components.

Examples of such analysis components include hemoglobin (Hb), albumin (Alb), globulin ($\alpha 1$, $\alpha 2$, $\beta$, and $\gamma$-globulin), fibrinogen, etc. The hemoglobin mentioned above includes plural hemoglobin types, such as normal hemoglobin (HbA), hemoglobin variants (HbC, HbD HbE, HbS, etc.), fetal hemoglobin (HbF), etc. Hemoglobin variants are known to cause various types of diseases and pathological conditions (for example, HbS causes sickle cell anemia), and so identifying hemoglobin types is expected to be helpful in diagnosing and treating diseases and pathological conditions. In the following explanation, explanation will be given of an example of a case in which the analysis components are hemoglobin (in particular, hemoglobin variant types). Normal adult hemoglobin is predominantly constituted by HbA, with only small amounts of HbF and HbA2 contained therein. Hemoglobin is a tetramer, and in the case of HbA, for example, is configured by two $\alpha$ chains and two $\beta$ chains. When a mutation arises in the genetic sequence responsible for the production of either the $\alpha$ chains or the $\beta$ chains, this results in the production of such chains being suppressed or chains being produced that differ from their normal amino acid sequence, giving rise to abnormal hemoglobin types. Generally, such hemoglobin types are referred to as hemoglobin variants. The genotype for hemoglobin in a normal person is HbA/HbA homozygous. However, the genotype of a carrier of a hemoglobin variant is either HbA/HbV heterozygous (where HbV is a given variant other than HbA) or HbV/HbV homozygous (or heterozygous if these HbV's are different from each other). In clinical laboratory testing, a blood specimen sourced from a normal person is referred to as an HbAA specimen, a blood specimen sourced from a person who is HbA/HbV heterozygous is referred to as an HbAV specimen (where V is a given variant), and a blood specimen sourced from a person who is HbV/HbV homozygous (or heterozygous if these HbV's are different from each other) is referred to as an HbVV specimen (where each V is a given variant). Thus, an HbAS specimen, for example, is predominantly constituted by HbA and HbS, with only small amounts of HbF and HbA2 contained therein. An HbSS specimen, for example, is predominantly constituted by HbS, with only small amounts of HbF and HbA2 contained therein.

Figure 2:
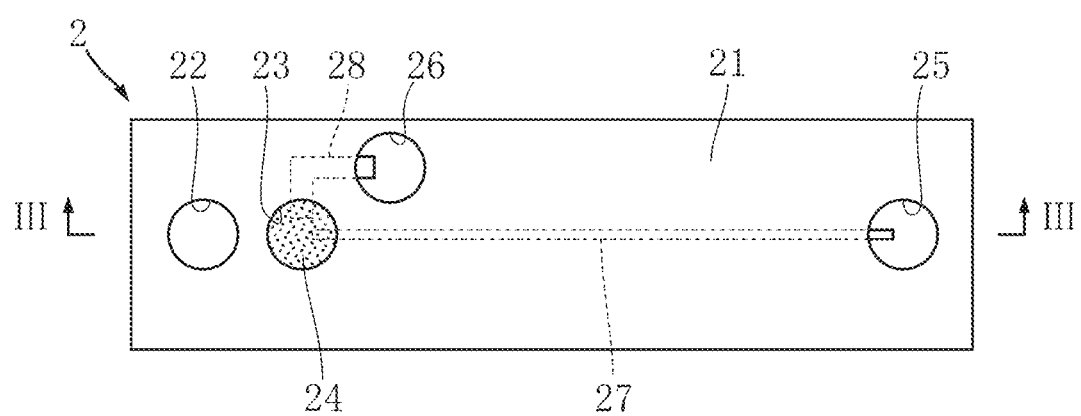
FIG. 2 is a plan view illustrating an analysis chip employed in the analytical system of FIG. 1.
Figure 3:
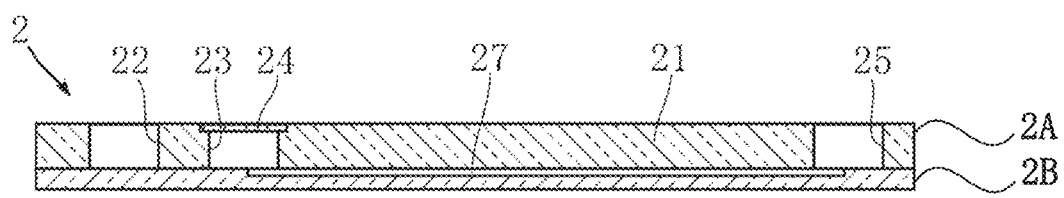
FIG. 3 is a cross-section taken along line of FIG. 2.

The analysis chip 2 retains the sample Sa, and provides a place for performing analysis on the target sample Sa in a state in which the analysis chip 2 has been loaded in the analysis device 1. In the present embodiment, the analysis chip 2 is configured by a so-called disposable type of analysis chip, in which the chip is meant to be disposed of after a single analysis has been completed. As illustrated in FIGS. 2 and 3, the analysis chip 2 includes a body 21, a mixing reservoir 22, an inlet reservoir 23, a filter 24, a waste reservoir 25, an electrode reservoir 26, a capillary channel 27, and a communication flow path 28. FIG. 2 is a plan view of the analysis chip 2, and FIG. 3 is a cross-section taken along line of FIG. 2. Note that the analysis chip 2 is not limited to a disposable type of chip, and the analysis chip 2 may be a chip that is employed for plural analyses. Further, the analytical system according to the present invention is not limited to configuration in which the analysis chip 2 is provided as a separate body loaded in the analysis device 1. The analytical system according to the present embodiment may be configured such that a functional part that accomplishes similar functionality to that of the analysis chip 2 is incorporated in the analysis device 1.

The body 21 is a stage for the analysis chip 2. The material of the body 21 is not particularly limited and examples thereof include glass, fused silica, plastic, etc. In the present embodiment, the body 21 is formed from separate bodies, these being an upper portion 2A and a lower portion 2B illustrated in FIG. 3, in a configuration in which the upper portion 2A and the lower portion 2B are joined to each other. Note that there is no limitation thereto, and, for example, the body 21 may be formed as a single integrated unit.

The mixing reservoir 22 is an example of a site where a mixing process is performed to mix the sample Sa and a dilution liquid Ld, described later. The mixing reservoir 22 is, for example, configured as a recess open to the upper side by a through hole formed in the upper portion 2A of the body 21. The inlet reservoir 23 is a reservoir for introducing a sample mixture Sm as a sample solution that was obtained from the mixing process in the mixing reservoir 22. The inlet reservoir 23 is, for example, configured as a recess open to the upper side by a through hole formed in the upper portion 2A of the body 21.

The filter 24 is provided to the opening of the inlet reservoir 23, with the opening serving as an example of an introduction path to the inlet reservoir 23. The specific configuration of the filter 24 is not limited, and preferable examples of the configuration include Cellulose Acetate Membrane Filters (manufactured by Advantec, 0.45 µm hole diameter).

The waste reservoir 25 is a reservoir that is positioned on the downstream side in the electroosmotic flow of the capillary electrophoresis technique. The waste reservoir 25 is, for example, configured as a recess open to the upper side by a through hole formed in the upper portion 2A of the body 21. The electrode reservoir 26 is a reservoir into which an electrode 31 is inserted in an analysis process of the capillary electrophoresis technique. The electrode reservoir 26 is, for example, configured as a recess open to the upper side by a through hole formed in the upper portion 2A of the body 21. The communication flow path 28 connects the inlet reservoir 23 and the electrode reservoir 26 together, and configures a conduction path between the inlet reservoir 23 and the electrode reservoir 26.

The capillary channel 27 is a micro flow path that connects the inlet reservoir 23 and the waste reservoir 25 together, and is a place where electroosmotic flow occurs in the capillary electrophoresis technique. The capillary channel 27 is configured as a groove formed in the lower portion 2B of the body 21. Note that a recess or the like may be formed in the body 21 as appropriate to promote illumination of light onto the capillary channel 27 and emission of light transmitted through the capillary channel 27. The size of the capillary channel 27 is not particularly limited; as an example, the capillary channel 27 has a width of from 25 µm to 100 µm, a depth of from 25 µm to 100 µm, and a length of from 5 mm to 150 mm. The overall size of the analysis chip 2 is appropriately set so as to accommodate the size of the capillary channel 27 and the size, placement, and so on of the mixing reservoir 22, the inlet reservoir 23, the waste reservoir 25, and the electrode reservoir 26.

Note that an analysis chip 2 with the above configuration is merely an example, and any analysis chip with a configuration capable of analyzing by an electrophoresis technique may be appropriately employed therefor.

The analysis device 1 performs analysis processing on the sample Sa, in a state in which the analysis chip 2 spotted with the sample Sa has been loaded in the analysis device 1. The analysis device 1 includes electrodes 31, 32, a light source 41, an optical filter 42, a lens 43, a slit 44, a detector 5, a dispenser 6, a pump 61, a dilution liquid reservoir 71, a migration liquid reservoir 72, and a control section 8. Note that the light source 41, the optical filter 42, the lens 43, and the detector 5 configure an example of what is referred to as a measurement section in the present embodiment.

The electrodes 31, 32 apply a predetermined voltage to the capillary channel 27 in the capillary electrophoresis technique. The electrode 31 is inserted into the electrode reservoir 26 of the analysis chip 2, and the electrode 32 is inserted into the waste reservoir 25 of the analysis chip 2. The voltage that is applied by the electrodes 31, 32 is not particularly limited, and may be from 0.5 kV to 20 kV, for example.

The light source 41 is a location where light is emitted for measuring absorbance as an optically measured value in the capillary electrophoresis technique. The light source 41 is provided, for example, with an LED chip that emits light of a predetermined wavelength range. The optical filter 42 attenuates light of predetermined wavelengths in the light from the light source 41 and transmits the light of other wavelengths therein. The lens 43 focuses light that has been transmitted through the optical filter 42 onto an analysis site of the capillary channel 27 of the analysis chip 2. The slit 44 removes excess light from the light focused using the lens 43 which might otherwise cause scattering and the like.

The detector 5 receives light transmitted through the capillary channel 27 of the analysis chip 2, and is configured by provision of a photodiode, a photo IC, etc.

As shown above, the path on which the light emitted from the light source 41 goes to the detector 5 is referred to as an optical path. Then, the optically measured value is measured as to the solution (i.e., either the sample solution or the migration liquid, or the mixture of both) flowing in the capillary channel 27 at a position where the optical path intersects the capillary channel 27. That is, the position in the capillary channel 27 where the optical path from the light source 41 to the detector 5 intersects is referred to as a measurement section for the optically measured value. The examples for optically measured value includes the absorbance. The absorbance indicates an extent to which the light in the optical path is absorbed by the solution flowing in the capillary channel 27. In other words, the absorbance is an absolute value of an common logarithm of a rate of a transmitted light intensity to an incident light intensity. In this case, a spectrophotometer for general use can be utilized as the detector 5. Note that, the optically measured value other than the absorbance, e.g., the transmitted light intensity alone, can be used for the present embodiment. Explanation will be made for a case in which the absorbance is used as the optically measured value as an example hereinafter.

The dispenser 6 dispenses a desired amount of the dilution liquid Ld and the migration liquid Lm, and the sample mixture Sm, and the dispenser 6 includes a nozzle, for example. The dispenser 6 can be freely moved between plural predetermined positions in the analysis device 1 using a drive mechanism, not illustrated in the drawings. The pump 61 is a drawing source to the dispenser 6 and a purge source from the dispenser 6. Further, the pump 61 may be employed as a drawing source as well as a purging source for ports, not illustrated in the drawings, provided to the analysis device 1. Such ports may be employed to fill the migration liquid Lm and the like. Further, a dedicated pump may also be provided separate to the pump 61.

The dilution liquid reservoir 71 is a reservoir for storing the dilution liquid Ld. The dilution liquid reservoir 71 may be a reservoir that is permanently installed to the analysis device 1, or may be a container that encloses a predetermined amount of the dilution liquid Ld and is loaded into the analysis device 1. The migration liquid reservoir 72 is a reservoir for storing the migration liquid Lm. The migration liquid reservoir 72 may be a reservoir that is permanently installed to the analysis device 1, or may be a container that encloses a predetermined amount of the migration liquid Lm and is loaded into the analysis device 1.

The dilution liquid Ld is mixed with the sample Sa to produce the sample mixture Sm as the sample solution. The main agent of the dilution liquid Ld is not particularly limited, and examples include water and saline, and preferable examples are liquids containing components resembling those of the migration liquid Lm, described later. Further, the dilution liquid Ld may have additives added to the main agent as required.

In the analysis process by the electrophoresis technique, the migration liquid Lm is filled into the waste reservoir 25 and the capillary channel 27, and is a medium in which to generate electroosmotic flow in the electrophoresis technique. Although the migration liquid Lm is not particularly limited, the migration liquid Lm preferably employs an acid. The acid is, for example, citric acid, maleic acid, tartaric acid, succinic acid, fumaric acid, phthalic acid, malonic acid, or malic acid. Further, the migration liquid Lm preferably includes a weak base. The weak base is, for example, arginine, lysine, histidine, Tris, or the like. The pH of the migration liquid Lm is, for example, a range of from pH 4.5 to pH 6. The type of buffer of the migration liquid Lm is MES, ADA, ACES, BES, MOPS, TES, HEPES, or the like. Similar to as explained above regarding the dilution liquid Ld, additives may also be added to the migration liquid Lm as required.

Although examples are shown below for the migration liquid Lm, the dilution liquid Ld and the sample mixture Sm, these are optionally selected from known agent if a change in the optically measured value caused by an arrival of an interface between the sample solution (sample mixture Sm) and the migration liquid (Lm) at an interface arrival time point described thereafter can occur in the combination of them.

(Migration Liquid Lm)

The migration liquid includes the following components, for example:

Citric acid: 40 mM
Sodium chondroitin sulfate C: 1.25% w/v
Piperazine: 20 mM
Polyoxyalkylene alkyl ether (product name: Emulgen LS-110, Kao): 0.1% w/v
Sodium azide: 0.02% w/v
Proclin 300: 0.025% w/v Other than the above components, dimethylaminoethanol for a pH adjustment was dropped to the migration liquid to be adjusted to pH 5.0.

(Dilution Liquid Ld)

The dilution liquid includes the following components, for example:

Citric acid: 38 mM
Sodium chondroitin sulfate C: 0.95% w/v
1-(3-Sulfopropyl) pyridinium hydroxide (NDSB-201): 475 mM
Sodium 2-morpholinoethanesulfonate (MES): 19 mM
Polyoxyalkylene alkyl ether (product name: Emulgen LS-110, Kao): 0.4% w/v
Sodium azide: 0.02% w/v
Proclin 300: 0.025% w/v Other than the above components, dimethylaminoethanol for a pH adjustment was dropped to the dilution liquid to be adjusted to pH 6.0.

(Sample Mixture Sm)

The sample mixture was prepared by adding 1.5 µL of the sample Sa to the 60 µL of the dilution liquid Ld.

The control section 8 controls each section of the analysis device 1. The control section 8 is, for example, provided with a CPU, memory, an interface, etc. Programs and various data for performing the analytical method according to the present embodiment, described later, are appropriately stored in the memory.

Figure 4:
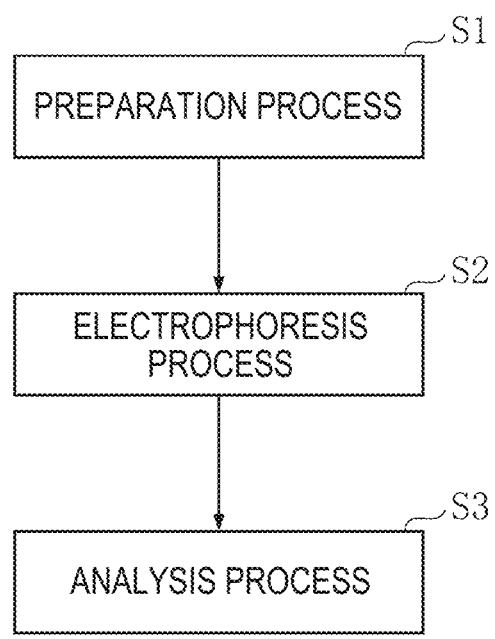
FIG. 4 is a flowchart illustrating an analytical method according to the embodiment of the present invention.

Next, explanation follows regarding an example of the analytical method according to the present invention performed employing the analytical system A1. FIG. 4 is a flowchart illustrating an analytical method in the present embodiment. The present analytical method includes a preparation process S1, an electrophoresis process S2, and an analysis process S3.

Preparation Process S1

Figure 5:
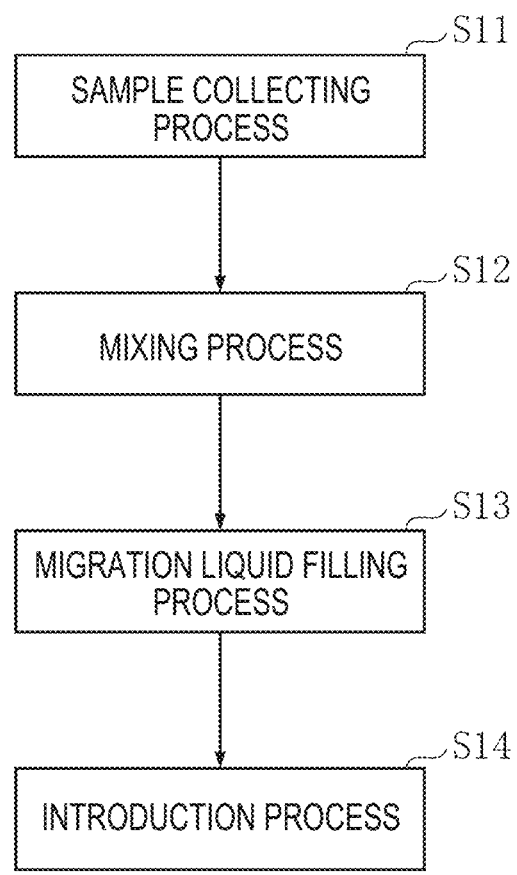
FIG. 5 is a flowchart illustrating a sequence of a preparation process.

FIG. 5 is a flowchart illustrating a specific sequence of the preparation process S1. As illustrated in FIG. 5, the preparation process S1 in the present embodiment includes a sample collecting process S11, a mixing process S12, a migration liquid filling process S13, and an introduction process S14.

Sample Collecting Process S11

First, the sample Sa is prepared. In the present embodiment, the sample Sa is blood collected from a human body. The blood may be whole blood, fractionated blood or blood that has undergone hemolysis, or the like. The analysis chip 2 onto which the sample Sa has been dispensed is loaded into the analysis device 1.

Mixing Process S12

Figure 6:
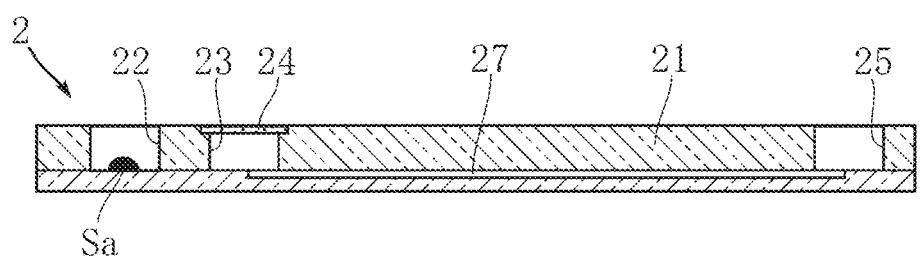
FIGS. 6 to 9 are cross-sections each illustrating a process in the preparation process of FIG. 5.
Figure 7:
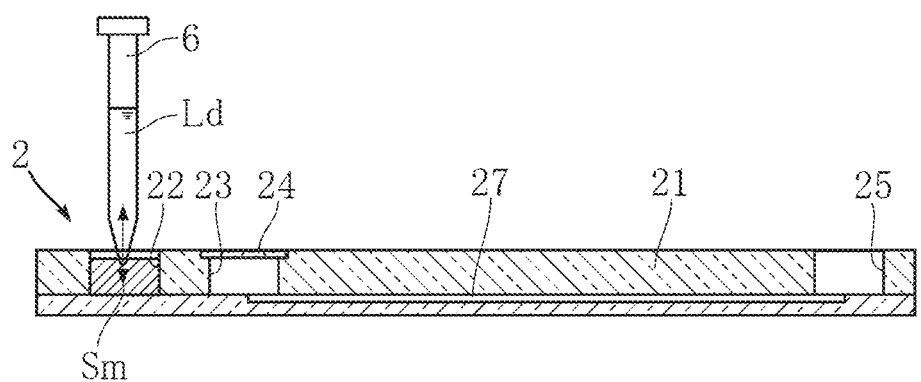

Next, the sample Sa and the dilution liquid Ld are mixed together. Specifically, as illustrated in FIG. 6, a predetermined amount of the sample Sa is spotted into the mixing reservoir 22 of the analysis chip 2. Next, a predetermined amount of the dilution liquid Ld in the dilution liquid reservoir 71 is drawn using the dispenser 6, and, as illustrated in FIG. 7, the predetermined amount of the dilution liquid Ld is dispensed into the mixing reservoir 22 of the analysis chip 2. Then, the dilution liquid Ld is repeatedly drawn in and purged out of the dispenser 6 using the pump 61 as a drawing source as well as a purging source. Thus, the sample Sa and the dilution liquid Ld are mixed together in the mixing reservoir 22, and the sample mixture Sm is thereby obtained. Mixing together of the sample Sa and the dilution liquid Ld may be performed using a method other than drawing and purging with the dispenser 6.

Migration Liquid Filling Process S13

Figure 8:
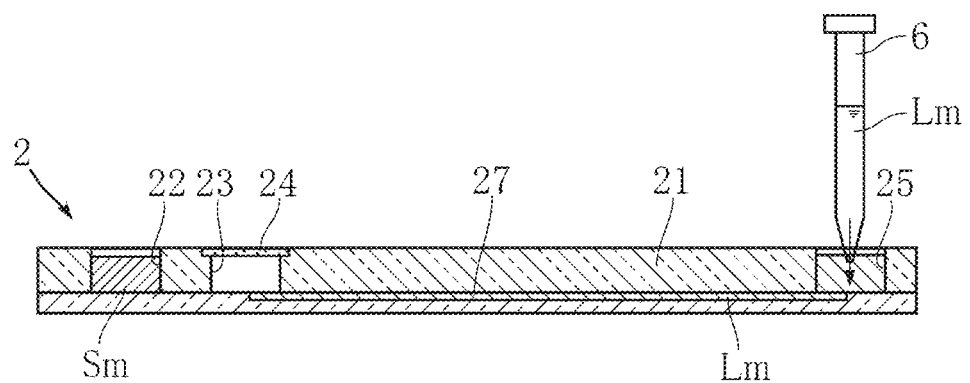

Next, the dispenser 6 is used to draw a predetermined amount of the migration liquid Lm in the migration liquid reservoir 72, and, as illustrated in FIG. 8, to dispense the predetermined amount of the migration liquid Lm into the waste reservoir 25 of the analysis chip 2. Then, the migration liquid Lm is filled into the waste reservoir 25 and the capillary channel 27 by using an appropriate technique, such as drawing in and purging out from the port as described above.

Introduction Process S14

Figure 9:
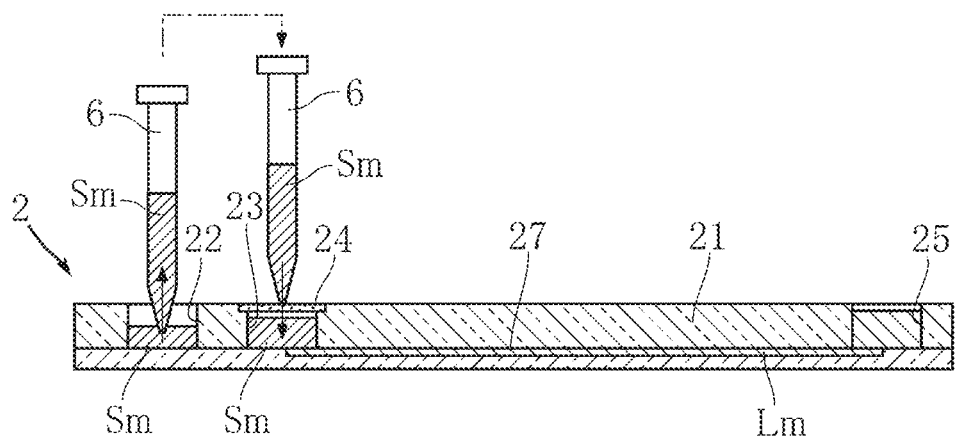
Figure 10:
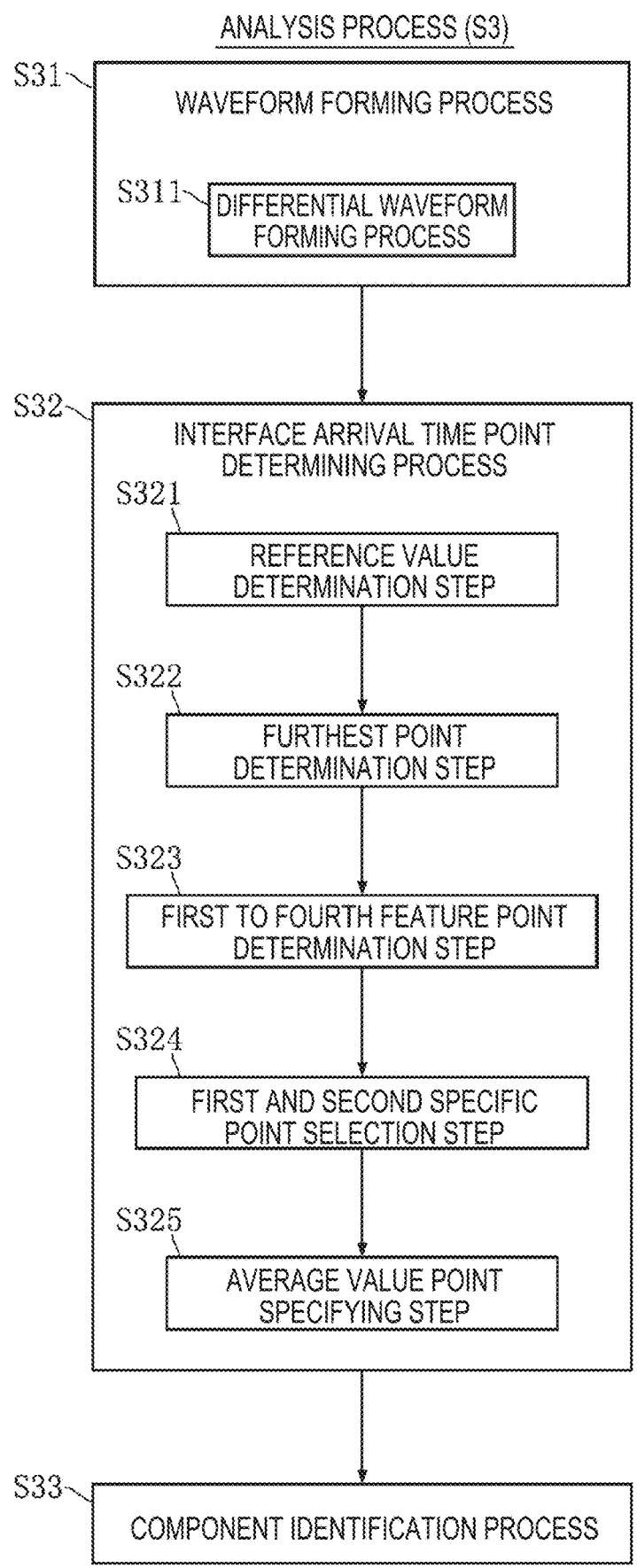
FIG. 10 is a flowchart illustrating a sequence of an analysis process.

Next, as illustrated in FIG. 9, a predetermined amount of the sample mixture Sm is collected from the mixing reservoir 22 using the dispenser 6. Then, the predetermined amount of sample mixture Sm is introduced from the dispenser 6 to the inlet reservoir 23. When introducing, the sample mixture Sm passes through the filter 24 provided at the opening of the inlet reservoir 23, this being an example of an introduction path to the inlet reservoir 23. Further, in the present embodiment, the sample mixture Sm passes from the inlet reservoir 23, through the communication flow path 28, and fills the electrode reservoir 26. When this occurs, the sample mixture Sm is caused to flow from the inlet reservoir 23 to the electrode reservoir 26 through the communication flow path 28. However, from the inlet reservoir 23 to the communication flow path 28, the sample mixture Sm flows in a direction substantially orthogonal to the length direction of the capillary channel 27 (see FIG. 2). On the other hand, the migration liquid Lm in the capillary channel 27 basically does not move at this stage. Since, as a result, a shear flow occurs at the section connecting the inlet reservoir 23 to the capillary channel 27 (see FIG. 3), a clear interface occurs between the sample mixture Sm and the migration liquid Lm. Note that any means, such as a movable filter physically provided at a boundary between the inlet reservoir 23 and the capillary channel 27, and a control of an alternation of a way of flowing, may be applied to the introduction process S14 if the interface occurs between the sample mixture Sm and the migration liquid Lm by the application of the means.

Electrophoresis Process S2

Next, as illustrated in FIG. 1, the electrode 31 is inserted into the electrode reservoir 26, and the electrode 32 is inserted into the waste reservoir 25. Then, voltage is applied to the electrodes 31, 32 under instruction from the control section 8. This voltage is, for example, from 0.5 kV to 20 kV. Thus, electroosmotic flow is induced, causing the sample mixture Sm to gradually move in the capillary channel 27, from the inlet reservoir 23 to the waste reservoir 25. When this is performed, the sample mixture Sm is filled in the inlet reservoir 23, and hemoglobin (Hb), this being the analysis component, is electrophoresed in a state in which the sample mixture Sm in the capillary channel 27 is continuously being supplied. When this is performed, the sample mixture Sm migrates through the capillary tube 27 while pushing the migration liquid Lm in the downstream direction, in a state in which the interface described above between the sample mixture Sm and the migration liquid Lm is maintained. Further, light emission from the light source 41 is started, and absorbance is measured by the detector 5. Then, the relationship is measured between the amount of time that has elapsed since the start of voltage application by the electrodes 31, 32 and the absorbance.

Analysis Process S3

An absorbance peak corresponding to a component in the sample mixture Sm having a comparatively fast movement speed appears at a time point when the elapsed time from the start of the voltage application is comparatively short. On the other hand, an absorbance peak corresponding to a component in the sample mixture Sm having a comparatively slow movement speed appears at a time point when the elapsed time from the start of the voltage application is comparatively long. Analysis (measurement of separation) is performed on the components in the sample mixture Sm by taking advantage of this fact. In the present embodiment, hemoglobin (hemoglobin variants in particular) contained in blood is analyzed, that is, the hemoglobin (hemoglobin variants) that could be contained in the sample mixture Sm (blood) are the components being subject to analysis. Analysis process S3 is executed under control of the control section 8 based on the measured absorbance. The analysis process S3 in the present embodiment includes a waveform forming process S31, an interface arrival time point determining process S32, and a component identification process S33.

Waveform Forming Process S31

Figure 11:
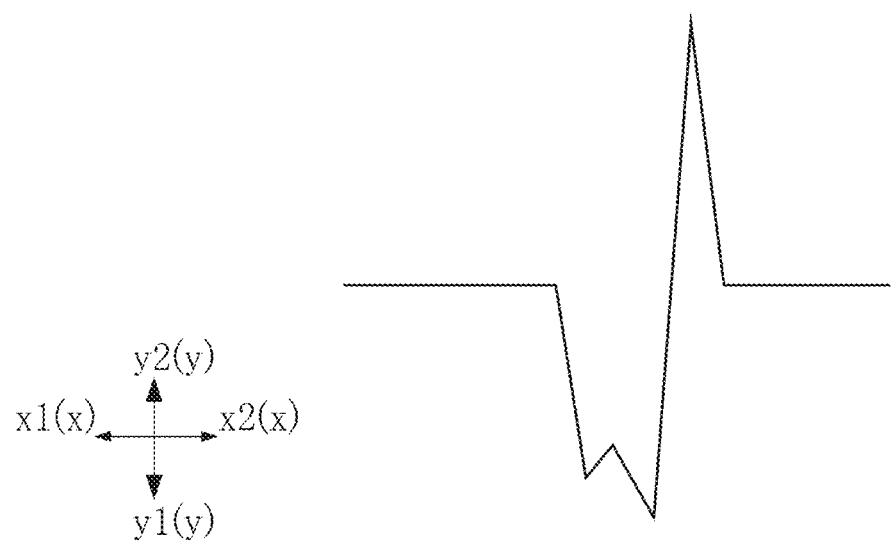
FIG. 11 is a graph illustrating an example of waveform data formed by a waveform forming process.

In the present process, an electropherogram is created by performing computation processing on the measured absorbance using the control section 8. Note that the measurement start time is the voltage application start time, and a measurement waveform related to the absorbance, which indicates the change in the optically measured value corresponding to the elapsed time after the measurement start time, is formed. The waveform forming process S31 in the present embodiment includes a differential waveform forming process S311. In the differential waveform forming process S311, a waveform of differential values is formed by taking the time derivative of the measured absorbance. FIG. 11 illustrates an example of a differential waveform formed by the differential waveform forming process S311. In the drawings, the x-axis is the time axis, and the y-axis is the differential value axis. In the following figures and explanation, a negative direction side along the time axis x is referred to as an x1 direction side, and a positive direction side along the time axis x is referred to as an x2 direction side. Similarly, a negative direction side along the differential value axis y is referred to as a y1 direction side, and a positive direction side along the differential value axis y is referred to as a y2 direction side.

Interface Arrival Time Point Determining Process S32

The interface arrival time point determining process S32 is a process in which the interface arrival time point as the time point after the voltage application is determined when the interface between the sample mixture Sm and the migration liquid Lm reaches the measurement section (i.e., the optical path) described above. Note that the interface may be measured at a measurement section (or an optical path) exclusive for the interface measurement if such a section is provided in addition to the measurement section (or the optical path) mentioned above. In the present analytical method and analytical system, a time point when the interface between the sample mixture Sm and the migration liquid Lm reaches at the measurement section described above is employed as a reference time point for timing in the component identification process S33 described later, instead of using the time point of the voltage application. According to the analysis conditions, such as the configuration of the capillary channel 27 in the analysis chip 2, the voltage applied by the electrodes 31, 32, etc., an empirical rule or a prior testing enables ascertainment of how much time elapses after applying voltage to the electrodes 31, 32 to the time point when the interface reaches the measurement section. Further, the interface is an interface between the sample mixture Sm and the migration liquid Lm, which do not have the same composition as each other, and thus functions similarly to an optical lens. Thus, some change in the optically measured value (e.g., the absorbance) can be seen when the interface reaches the measurement section. Such change appears as a change in the differential value appearing in plural typical differential waveforms described below (cf. FIGS. 13, 19, 21 and 23) due to components assumed to be included in the sample Sa, properties of the dilution liquid Ld and the migration liquid Lm, and a basic configuration of the analysis chip 2. Thus, the change appearing in the waveform is caused by the arrival of the interface between the sample mixture Sm as the sample solution and the migration liquid Lm. The present analytical method and the analytical system A1 determine the interface arrival time point based on the change appearing in the waveform as the change in the optically measured value. Note that the change caused by the arrival of the interface between the sample solution and the migration liquid may be detected, not always based on the change appearing in the waveform, but by applying the transmitted light intensity itself or the change thereof, the absorbance value or the change thereof, or the means determining time change rate such as the change in the differential value instead of the differential waveform.

The interface arrival time point determining process S32 in the present embodiment includes a reference value determination step S321, a furthest point determination step S322, a first to fourth feature point determination step S323, a first and second specific point selection step S324, and an average value point specifying step S325.

Reference Value Determination Step S321

Figure 12:
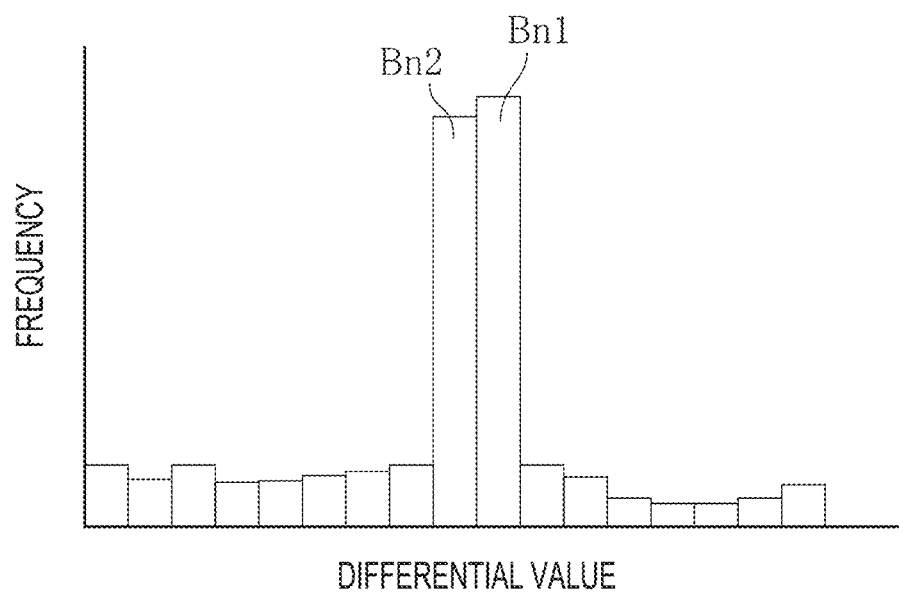
FIG. 12 is a histogram for finding a reference value.
Figure 13:
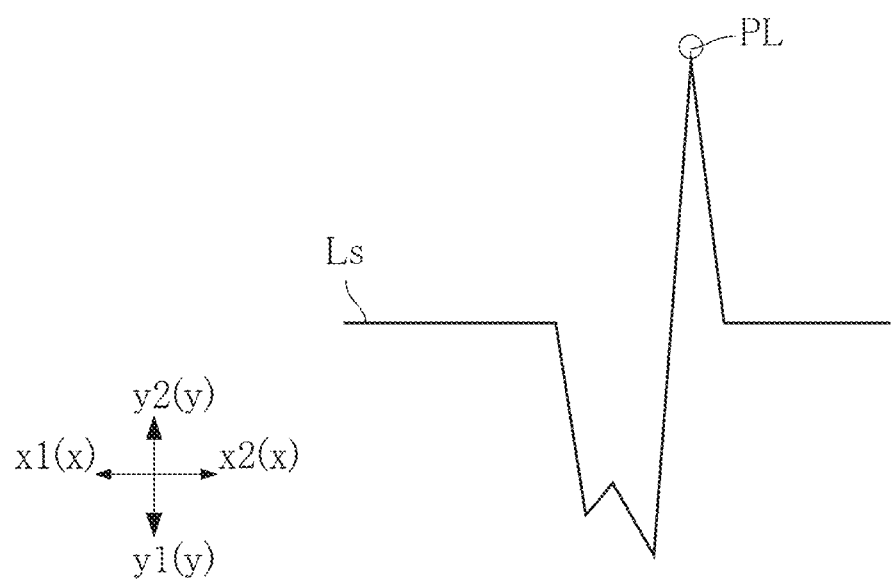
FIG. 13 is a graph illustrating determination of a furthest point.

The reference value determination step S321 is a step in which a reference value is determined to act as a reference for the waveform values (differential values) in a time range (for example, a duration of several seconds) presumed to include the interface arrival time point. FIG. 11 illustrates a waveform in the time range. The reference value determination step S321 in the present embodiment creates a histogram in which, as illustrated in FIG. 12, the frequencies of the differential values of the differential waveform are shown on the vertical axis. Then, bin Bn1 is identified as the most frequent bin. Next, bin Bn2 is identified as the bin with the higher frequency among the two bins adjacent to the bin Bn1. Then, for example, a reference value Ls which will be a reference for the differential values is determined by taking a weighted average of the frequencies and differential values of the bin Bn1 and the bin Bn2. For example, as illustrated in FIG. 13, the reference value Ls roughly corresponds to the horizontal line segment extending left to right. Strictly speaking, the reference value Ls may be a value that slightly differs from that of this horizontal segment. However, in the following explanation, explanation will be regarding an example of a case that assumes such a difference to be an error that can be ignored, and the horizontal segment is taken as being equivalent to the reference value Ls.

Furthest Point Determination Step S322

Next, the furthest point determination step S322 is performed. On the present step, as illustrated in FIG. 13, the point in the time range, described above, at which the differential value is the furthest from the reference value Ls determined on the reference value determination step S321 is determined. In the example illustrated, the point furthest from the reference value Ls in the y2 direction is determined to be a furthest point PL.

First to Fourth Feature Point Determination Step S323

Figure 14:
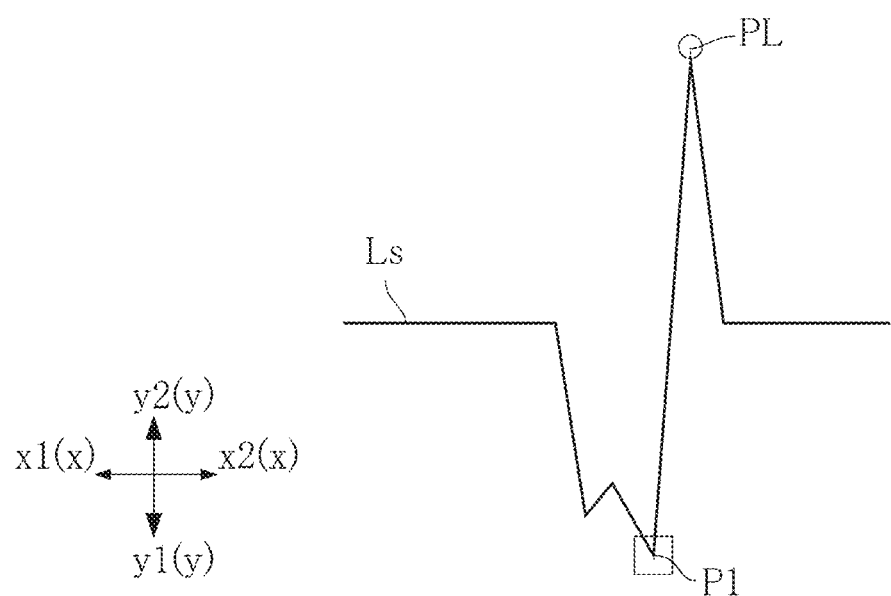
FIG. 14 is a graph illustrating determination of a first feature point.

Next, the first to fourth feature point determination step S323 is performed. First, as illustrated in FIG. 14, referencing the furthest point PL (in other words, using the reference value Ls as a reference), a point having the furthest value at the y1 direction side is found within a predetermined search time range. The predetermined search time range is set to a time range in which a change in the waveform as a result of the presence of the interface could occur, and is appropriately set according to the analytical method and the analytical system. In the present embodiment, the predetermined search time range is approximately from 0.3 seconds to 1.5 seconds, for example. Accordingly, a first feature point P1 is a point that may be present either at the x1 direction side or at the x2 direction side of the furthest point PL. In the example illustrated, a point located at the x1 direction side of the furthest point PL and located at the y1 direction side of the reference value Ls is determined to be the first feature point P1.

Figure 15:
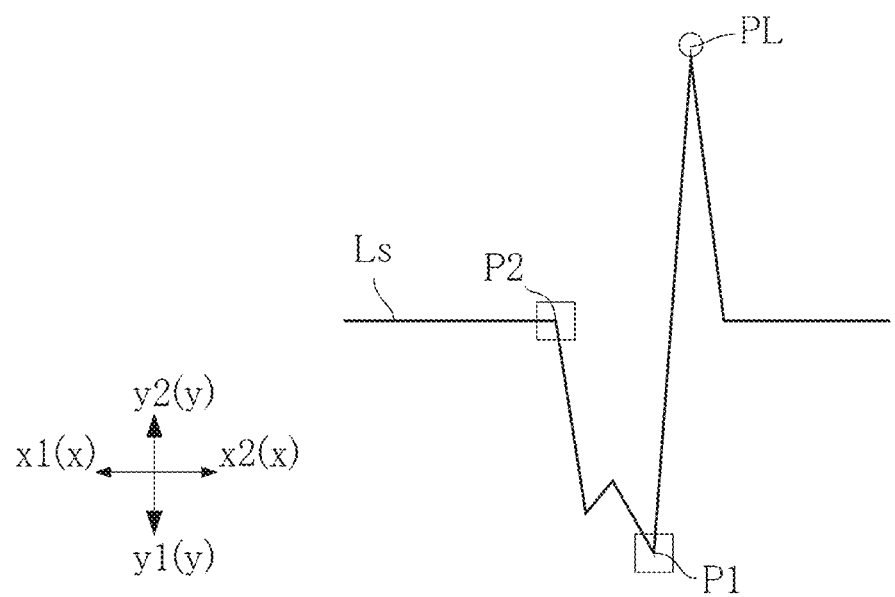
FIG. 15 is a graph illustrating determination of a second feature point.

Next, as illustrated in FIG. 15, with reference to the first feature point P1, a point having the furthest value at the y2 direction side is found at the x1 direction side within the predetermined search time range. In the example illustrated, heading in the x1 direction from the first feature point P1, the differential values substantially increase until it reaches the reference value Ls. Thus, when tracking in the x1 direction along the waveform from the first feature point P1, the first point to have a value close to the reference value Ls is determined to be a second feature point P2.

Figure 16:
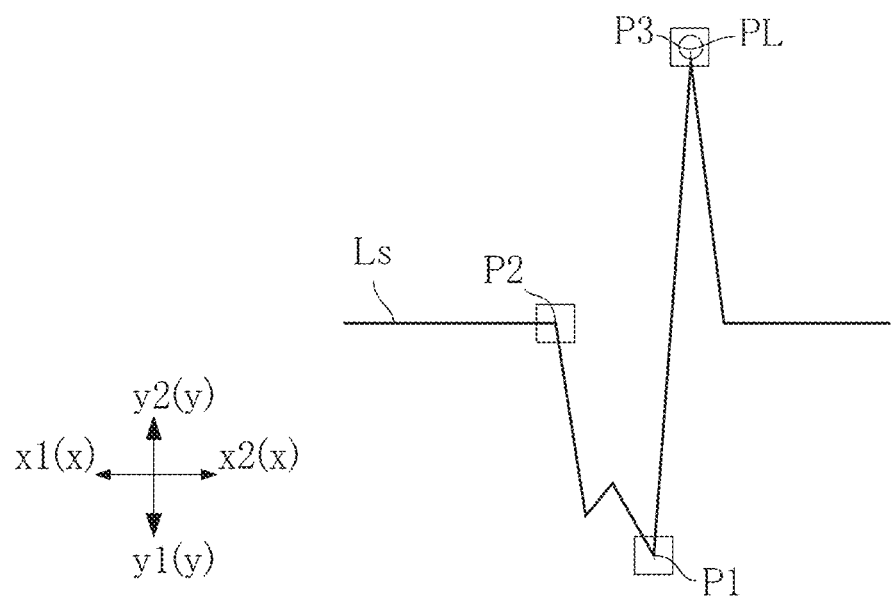
FIG. 16 is a graph illustrating determination of a third feature point.
Figure 17:
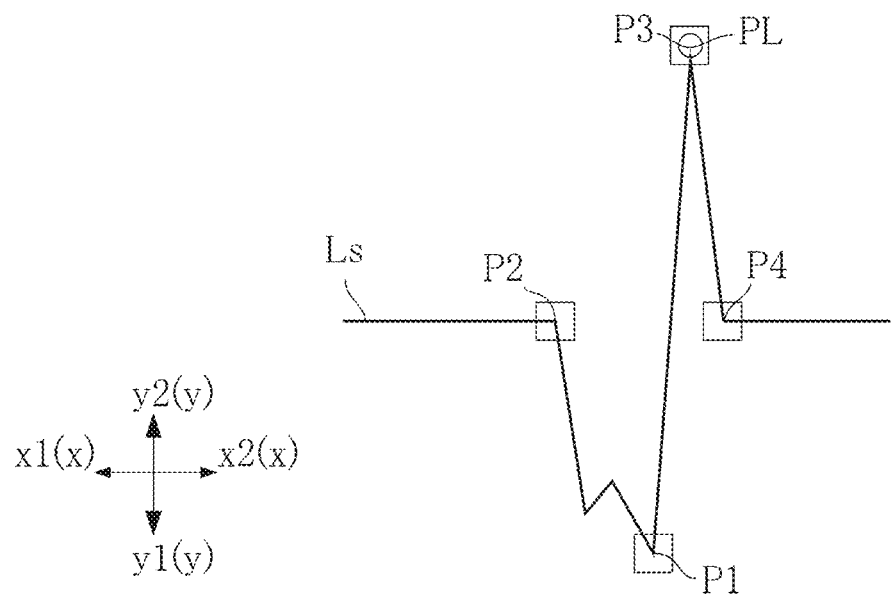
FIG. 17 is a graph illustrating determination of a fourth feature point.

Next, as illustrated in FIG. 16, with reference to the first feature point P1, the point having the furthest value at the y2 direction side is found at the x2 direction side within the predetermined search time range. In the example illustrated, the point already determined to be the furthest point PL corresponds to this point, and so is determined to be a third feature point P3. Next, as illustrated in FIG. 17, with reference to the third feature point P3, the point having the furthest value at the y1 direction side is found at the x2 direction side within the predetermined search time range. In the present example, a point having substantially the same value as that of the reference value Ls is determined to be a fourth feature point P4, and, for the sake of convenience, an inflection point on the differential waveform is selected therefor.

First and Second Specific Point Selection Step S324

Figure 18:
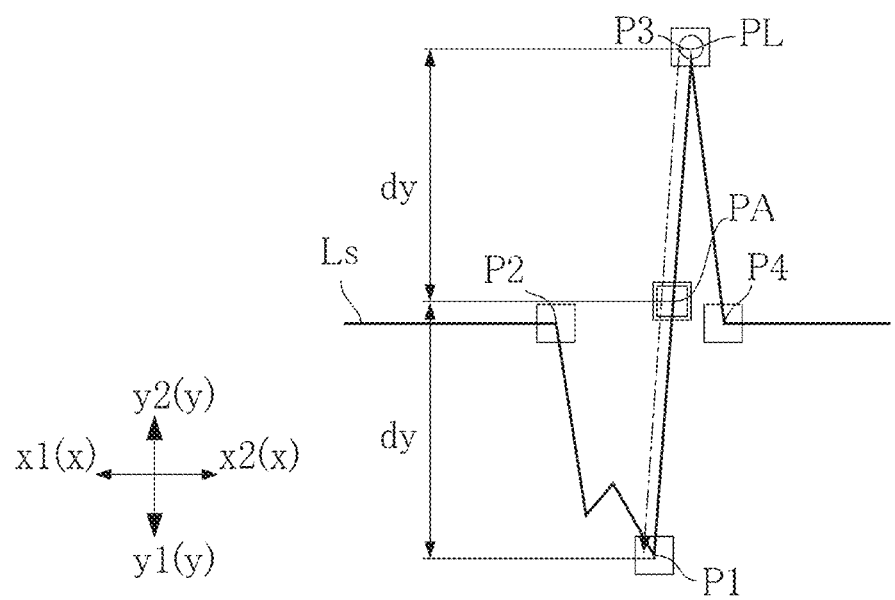
FIG. 18 is a graph illustrating determination of an average value point.

Next, the first and second specific point selection step S324 is performed. On this step, as illustrated in FIG. 18, a first specific point and a second specific point are selected from the first feature point P1 to the fourth feature point P4. The selection of the first specific point and the second specific point is performed by, for example, a basic policy of selecting a combination of the two points that have the largest difference in differential values (values on the differential value y axis) from each other. Examples will be given regarding this specific technique. First, the values of the second feature point P2 and the third feature point P3 are compared. In the present example, the value of the third feature point P3 is larger than the value of the second feature point P2. Thus, the third feature point P3 is therefore selected to be the first specific point. Next, a decision is made as to whether or not the value of the first feature point P1 is significantly smaller than the reference value Ls. This decision is made, for example, by comparing the difference between the reference value Ls and the value of the first feature point P1, which is lower than the reference value Ls, against a 5% value of the difference between the value of the third feature point P3 and the reference value Ls. When the difference between the reference value Ls and the value of the first feature point P1 is larger than the 5% value of the difference between the value of the third feature point P3 and the reference value Ls, the first feature point P1 is determined to be significantly smaller than the reference value Ls, and it is determined that the graph forms a distinct valley at the first feature point P1. As a result, the first feature point P1 is selected as the second specific point.

Average Value Point Specifying Step S325

Next, the average value point specifying step S325 is performed. On this step, the point is found that has an average value of the differential values of the third feature point P3 and the first feature point P1, which serve as the first specific point and the second specific point. In the present embodiment, tracking the differential waveform from a start point that is located at the x2 direction side of the time x-axis among the first specific point and the second specific point, the first point between the first specific point and the second specific point is found which has an average value of the first specific point and the second specific point. Thus, in the example illustrated, the point that is approximately the midpoint between the first feature point P1 and the third feature point P3 is determined to be an average value point PA. Namely, the difference in the differential values of the third feature point P3 and the average value point PA, and the difference in the differential values of the average value point PA P1 and the first feature point, are both equal to a value dy.

In the interface arrival time point determining process S32, when the average value point PA has been determined, the time point of the average value point PA is determined to be the interface arrival time point. The control section 8 performs processing such as appropriately storing the interface arrival time point in the memory, and utilizes the interface arrival time point in a subsequent analysis process.

FIGS. 19 to 24 illustrate an example of the interface arrival time point determining process S32 performed on other differential waveforms formed by the differential waveform forming process S311 in the waveform forming process S31.

Figure 19:
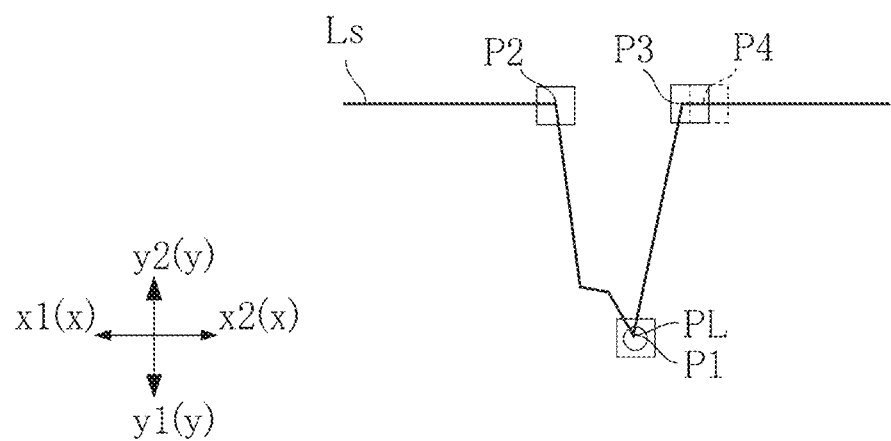
FIGS. 19 to 24 are graphs illustrating other examples of waveform data.

In the waveform illustrated in FIG. 19, on the furthest point determination step S322, the furthest point PL located at the y1 direction side, with reference to the reference value Ls that was determined on the reference value determination step S321 (in other words, using the reference value Ls as a reference), is determined to be the point furthest from the reference value Ls. Next, on the first to fourth feature point determination step S323, the point located furthest at the y1 direction side within the predetermined search time range with reference to the furthest point PL is determined to be the first feature point P1. In the present example, the furthest point PL is determined to be the same point as the first feature point P1. Next, a point that is located at the x1 direction side of the first feature point P1 and is the furthest at the y2 direction side is determined to be the second feature point P2. In the present example, the second feature point P2 is a point having substantially the same value as the reference value Ls, and for the sake of convenience, an inflection point of the differential waveform is selected therefor. Next, a point that is located at the x2 direction side of the first feature point P1 and is the furthest at the y2 direction side is determined to be the third feature point P3. In the present example, the third feature point P3 is a point having substantially the same value as the reference value Ls, and in the example illustrated, for the sake of convenience, an inflection point of the differential waveform is selected therefor. Next, a point that is located at the x2 direction side of the third feature point P3 and is the furthest at the y1 direction side is determined to be the fourth feature point P4. In the present example, for the sake of convenience, a point that is the same point as the third feature point P3 is determined to be the fourth feature point P4.

Figure 20:
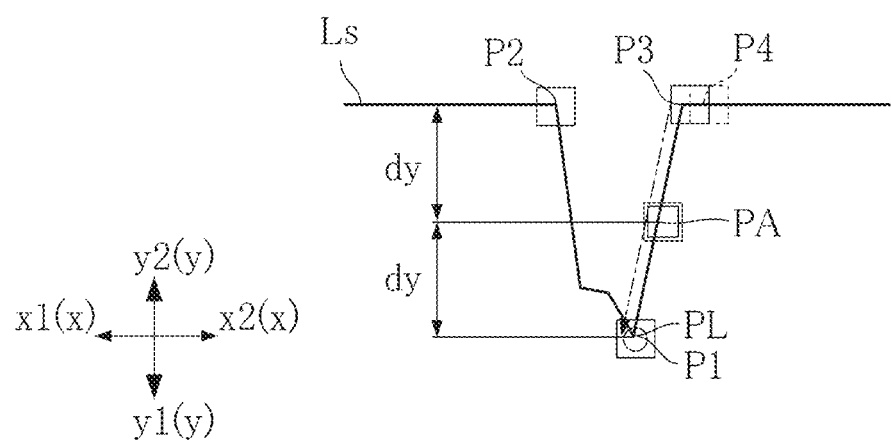

Next, as illustrated in FIG. 20, on the first and second specific point selection step S324, the first specific point and the second specific point are selected. Similarly to in the example described above, first, the values of the second feature point P2 and the third feature point P3 are compared. In the present example, the value of the second feature point P2 and the value of the third feature point P3 are substantially the same value. In such cases, for the sake of convenience, the third feature point P3 is selected to be the first specific point. Next, a decision is made as to whether or not the value of the first feature point P1 is significantly smaller than the reference value Ls. This decision is made, for example, by comparing the difference between the reference value Ls and the value of the first feature point P1, this being a value below the reference value Ls, against a 5% value of the difference between the value of the third feature point P3 and the reference value Ls. When the difference between the reference value Ls and the value of the first feature point P1 is larger than the 5% value of the difference between the value of the third feature point P3 and the reference value Ls, the first feature point P1 is determined to be significantly smaller than the reference value Ls, and it is decided that the graph forms a distinct valley at the first feature point P1. As a result, the first feature point P1 is selected as the second specific point. Then, on the average value point specifying step S325, tracking the differential waveform from the third feature point P3 as a start point that is located at the x2 direction side of the time x-axis among the first feature point P1 and the third feature point P3, the first point that has an average value of the first specific point and the second specific point is determined to be an average value point PA. The time point of the average value point PA is determined to be the interface arrival time point in the present example.

Figure 21:
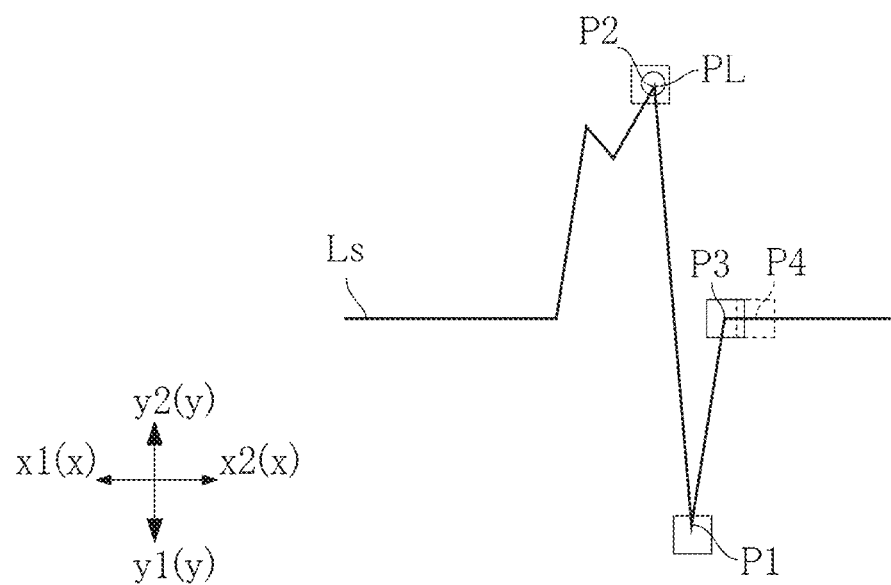

In the waveform illustrated in FIG. 21, on the furthest point determination step S322, the furthest point PL located at the y2 direction side with reference to the reference value Ls determined on reference value determination step S321 is determined to be the point furthest from the reference value Ls. Next, on the first to fourth feature point determination step S323, the point within the predetermined search time range that is located furthest at the y1 direction side with reference to the furthest point PL (in other words, using the reference value Ls as a reference) is determined to be the first feature point P1. In the present example, the point located at the x2 direction side of the furthest point PL is selected to be the first feature point P1. Next, the point that is located at the x1 direction side of the first feature point P1 and is the furthest at the y2 direction side is determined to be the second feature point P2. In the present example, the furthest point PL is determined to be the second feature point P2. Next, the point that is located at the x2 direction side of the first feature point P1 and is the furthest at the y2 direction side is determined to be the third feature point P3. In the present example, the third feature point P3 is a point having substantially the same value as the reference value Ls, and in the example illustrated, for the sake of convenience, an inflection point of the differential waveform is selected therefor. Next, the point that is located at the x2 direction side of the third feature point P3 and is the furthest at the y1 direction side is determined to be the fourth feature point P4. In the present example, for the sake of convenience, the same point as the third feature point P3 is determined to be the fourth feature point P4.

Figure 22:
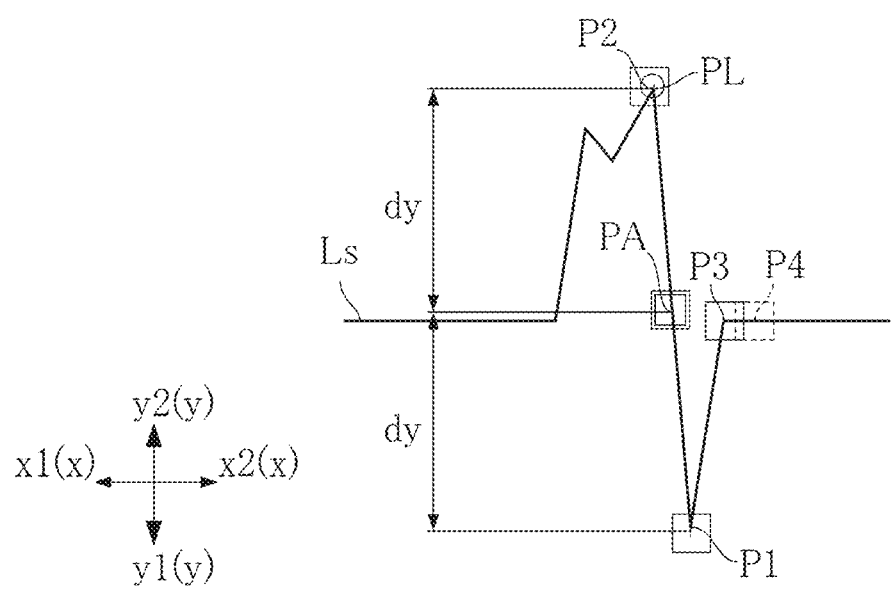

Next, as illustrated in FIG. 22, the first specific point and the second specific point are selected on the first and second specific point selection step S324. As described above, in the comparison of the values of the second feature point P2 and the third feature point P3, the value of the second feature point P2 is larger than the value of the third feature point P3. The second feature point P2 is accordingly selected to be the first specific point. Since the second feature point P2 is the point located the furthest at the x1 direction side of the time x-axis, the first feature point P1 is the only adjacent feature point, thus the first feature point P1 being selected as the second specific point. Then, on the average value point specifying step S325, tracking the differential waveform from the first feature point P1 as a start point that is located at the x2 direction side of the time x-axis among the first feature point P1 and the second feature point P2, the first point that has an average value of the first specific point and the second specific point is determined to be an average value point PA. The time point of the average value point PA is determined to be the interface arrival time point in the present example.

Figure 23:
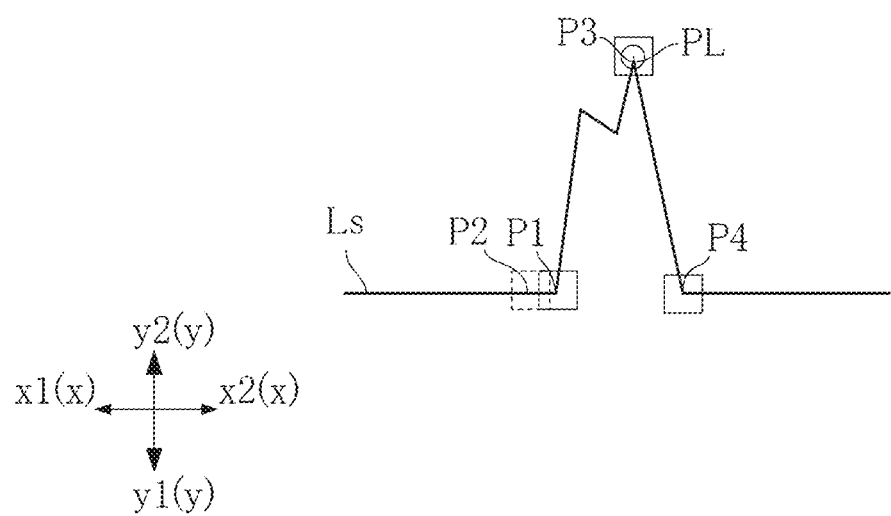

In the waveform illustrated in FIG. 23, with reference to the reference value Ls that was determined on the reference value determination step S321, on the furthest point determination step S322, the point that is the furthest from the reference value Ls is determined to be the furthest point PL located at the y2 direction side. Next, on the first to fourth feature point determination step S323, the point that is located furthest at the y1 direction side within the predetermined search time range with reference to the furthest point PL (in other words, using the reference value Ls as a reference) is determined to be the first feature point P1. In the present example, the first feature point P1 is a point having substantially the same value as the reference value Ls, and in the example illustrated, for the sake of convenience, an inflection point of the differential waveform is selected therefor. Next, a point that is located at the x1 direction side of the first feature point P1 and is at the y2 direction side is determined to be the second feature point P2. In the present example, for the sake of convenience, the same point as the first feature point P1 is determined to be the second feature point P2. Next, a point that is located at the x2 direction side of the first feature point P1, and is the furthest at the y2 direction side is determined to be the third feature point P3. In the present example, the same point as the furthest point PL is determined to be the third feature point P3. Next, a point that is located at the x2 direction side of the third feature point P3 and is the furthest at the y1 direction side is determined to be the fourth feature point P4. In the present example, the fourth feature point P4 is a point having substantially the same value as the reference value Ls, and in the example illustrated, for the sake of convenience, an inflection point of the differential waveform is selected therefor.

Figure 24:
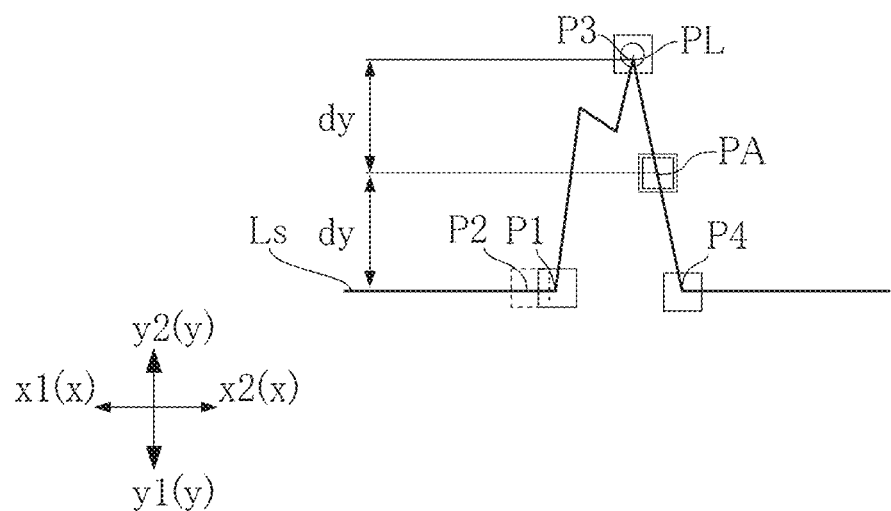

Next, as illustrated in FIG. 24, the first specific point and the second specific point are selected on the first and second specific point selection step S324. As described above, in a comparison of the values of the second feature point P2 and the third feature point P3, the value of the third feature point P3 is larger than the value of the second feature point P2. The third feature point P3 is accordingly selected to be the first specific point. Next, a decision is made as to whether or not the value of the first feature point P1 is significantly smaller than the reference value Ls. This decision is made, for example, by comparing the difference between the reference value Ls and the value of the first feature point P1, this being a value below the reference value Ls, against a 5% value of the difference between the value of the third feature point P3 and the reference value Ls. In the present example, since the first feature point P1 is substantially the same value as the reference value Ls, the difference between the reference value Ls and the first feature point P1 is smaller than the 5% value of the difference between the value of the third feature point P3 and the reference value Ls. Therefore, the first feature point P1 is not determined to be significantly smaller than the reference value Ls, and it is not decided that the graph forms a distinct valley at the first feature point P1. As a result, the fourth feature point P4 is selected to be the second specific point. Then, on the average value point specifying step S325, tracking the differential waveform from the fourth feature point P4 as a start point that is located at the x2 direction side of the time x-axis among the third feature point P3 and the fourth feature point P4, the first point between the first specific point and the second specific point that has the average value of the first specific point and the second specific point is determined to be the average value point PA. The time point of the average value point PA is determined to be the interface arrival time point of the present example.

Component Identification Process S33

In the present process, the relationship between the elapsed time from the start of the voltage application and the optically measured value such as the absorbance, and the interface arrival time point obtained in the interface arrival time point determining process S32 described above, are used to identify components contained in the sample solution. Otherwise, the components contained in the sample solution may be identified using the optically measured value such as the absorbance at the elapsed time from the interface arrival time point. Note that the relationship between the elapsed time from the start of the voltage application and the absorbance is expressed as the measured waveform as obtained in the waveform forming process S31 described above, which may be used therefor. For example, for the measurement waveform obtained in the waveform forming process S31, the time axis is assumed to be the elapsed time from the interface arrival time point. Then, the components contained in the sample Sa are identified by comparing the configuration of plural peak waveform portions appearing in this waveform against base waveform data prepared in advance for each component among the components that could be contained in the sample mixture Sm (sample Sa). Such base waveform data is, for example, stored in the memory of the control section 8. Note that identification using the base waveform data is merely a specific example of the identification technique of the component identification process S33, and the specific technique is not limited as long as the identification technique used the interface arrival time point as the reference.

Next, explanation follows regarding operation of the analytical method and the analytical system A1 in the present embodiment.

According to the present embodiment, the time point when the interface between the sample mixture Sm as a sample solution and the migration liquid Lm reaches the measurement section is determined to be the interface arrival time point, and this interface arrival time point is used to perform the component identification process. This enables the time point of the reference in the component identification process to appropriately conform to the actual timing of interface arrival even if the arrival of the interface were to be slightly ahead or behind on the time axis as a result of, for example, differences in the specific configuration of the analysis chip 2 or the analysis conditions. The event referred to as the arrival of the interface has a significant and reliable association to the subsequent arrival of various specific components, and the positions on the time axis of the waveforms corresponding to their arrivals. Accordingly, identification error in the component identification process caused by inaccuracy in a reference time can be suppressed, and analysis can be performed with greater accuracy.

Figure 25:
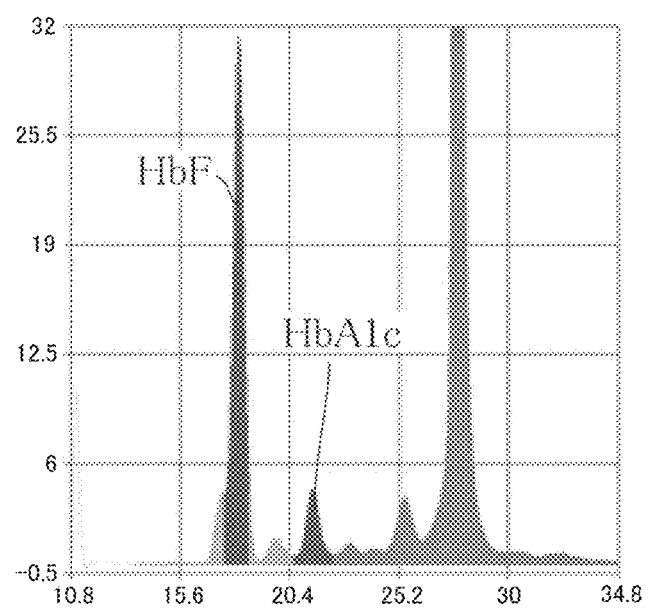
FIG. 25 is a graph illustrating a result of a component identification process of the embodiment of the present invention.
Figure 26:
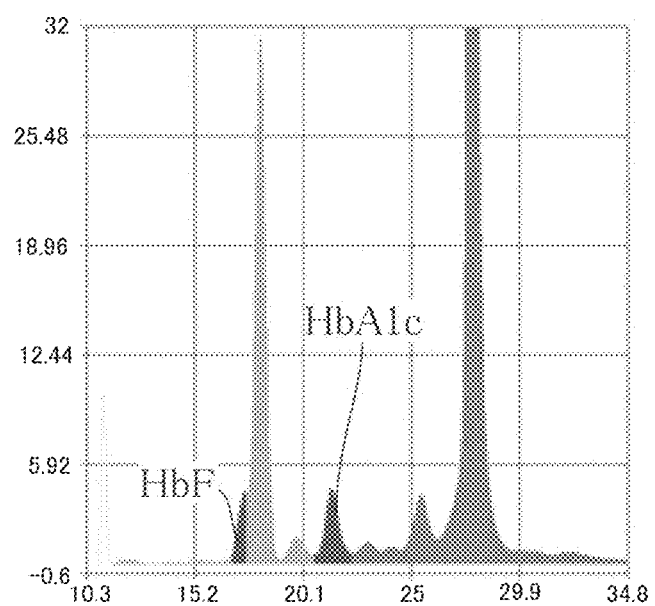
FIG. 26 is a graph illustrating a result of a component identification process of a comparative example.

FIG. 25 illustrates an Example of the component identification process S33 in the present embodiment. In the present example, the peaks for HbF and HbA1c are identified by being in a precise range of their correct positions on the time axis by using the interface arrival time point determined in the interface arrival time point determining process S32. On the other hand, FIG. 26 illustrates identification results of the component identification process S33 of a Comparative Example. In this Comparative Example, the time point of the furthest point PL is employed as the interface arrival time point itself, resulting in a time point shifted by 0.5 seconds from the correct interface arrival time point being employed as the interface arrival time point in component identification process S33. This leads to a peak at an incorrect position different from that in FIG. 25 being identified as the peak for HbF as a result of this error in the interface arrival time point. Further, the peak of the HbA1c is identified by the peak at substantially the same position as the peak in FIG. 25. However, in the Comparative Example (FIG. 26) in which the time point of the furthest point PL is employed as the interface arrival time point itself, the HbA1c measurement value is 4.89%, and the HbA1c value in the Example (FIG. 25) in the present embodiment is 5.36%, and so the HbA1c measurement value contains an error of 0.47%. The cause of this error is thought to be as described below. First, identification of the peak for HbA1c is found based on the ratio of the integrated area value of the HbA1c peak against the area value of the total HbA. Here, the area value of HbF is not included in the area value of the total HbA. It is therefore thought that error is contained in the HbA1c measurement value due to change in the area value of the total HbA as a result of incorrect recognition of HbF. Accordingly, determining the interface arrival time point by the interface arrival time point determining process S32 in the present embodiment enables the component identification process S33 to be executed with greater accuracy.

Further, in the interface arrival time point determining process S32, the differential waveform of the absorbance is used to determine the interface arrival time point by executing the differential waveform forming process S311 in the waveform forming process S31. The differential waveform is able to show changes in the absorbance due to arrival of the interface more sharply. This enables the interface arrival time point to be determined with greater accuracy.

The first specific point and the second specific point are selected on the first and second specific point selection step S324, and by employing the technique on the average value point specifying step S325 of determining the point having the average value of the first specific point and the second specific point, the interface arrival time point can be determined with greater accuracy based on the peak caused by the interface appearing in the differential waveform.

Further, the reference value Ls is determined on reference value determination step S321, and the furthest point PL is determined with reference to the reference value Ls on the furthest point determination step S322.

The first feature point P1 to the fourth feature point P4 are determined with reference to the furthest point PL (in other words, using the reference value Ls as a reference) on the first to fourth feature point determination step S323. There is a rational logic for the actual time point when the interface reached, or an appropriate time point assumed as the time point when the interface reached, to fall within the predetermined search time range with reference to the furthest point PL. Then, as to the various typical differential waveforms illustrated in FIG. 11 (FIG. 17), FIG. 19, FIG. 21, and FIG. 23, characteristic points can be determined objectively and automatically without subjectivity by determining the first feature point P1 to the fourth feature point P4 with reference to the furthest point PL (in other words, using the reference value Ls as a reference). This means that, for performing automatic analysis in which the analytical system A1 is used with various samples, more accurate analysis can properly be performed with greater reproducibility, not owing to the skill and experience of the user, for example.

Selecting the first specific point and the second specific point among the first feature point P1 to the fourth feature point P4 applies more accurate analysis execution automatically and with good reproducibility. When determining the average value point PA to have the average value of the first specific point and the second specific point on the average value point specifying step S325, the average value point PA can be determined with good reproducibility even if small and partial peaks are contained within the predetermined detection time range by finding the average value point PA using a start point located at either side (the x2 direction side in the examples described above) of the time x-axis.

Although the furthest two points along the differential value axis among the first to fourth feature points are selected as the first and second specific points in the above embodiment, any two points among the feature points that separates further than a predetermined interval may be selected as the first and second specific points even if they are not the furthest two points.

The analytical method and the analytical system according to the present invention are not limited by the present embodiment described above. Specific configuration of the analytical method and the analytical system according to the present invention may be subjected to various design changes.

What is claimed is:

1. An analytical method for analyzing a component contained in a sample solution by using capillary electrophoresis, comprising:
   a process of introducing the sample solution to a micro flow path filled with a migration liquid;
   a process of determining an interface arrival time point when an interface between the sample solution and the migration liquid reaches a predetermined measurement position of the micro flow path;
   a process of determining a component arrival time point when the component reaches the predetermined measurement position of the micro flow path; and
   a process of identifying the component based on an elapsed time from the interface arrival time point to the component arrival time point.

2. The analytical method of claim 1, wherein the sample solution is a solution containing blood as the sample, and the component is hemoglobin.

3. The analytical method of claim 1, further comprising a process of measuring an optically measured value corresponding to an elapsed time after applying a voltage to the micro flow channel, wherein the interface arrival time point is determined based on the optically measured value.

4. The analytical method of claim 3, wherein:
   the optically measured value is an absorbance of the sample solution;
   a process of forming a waveform related to the absorbance corresponding to the elapsed time after applying the voltage to the micro flow path is performed before the process of determining the interface arrival time point.

5. The analytical method of claim 4, comprising:
   a step of differentiating the waveform with respect to time to obtain differential values and form a differential waveform in which the differential values corresponding to the elapsed time are expressed; and
   the differential waveform is used in the process of determining the interface arrival time point.

6. The analytical method of claim 5, wherein the process of determining the interface arrival time point includes:
   a step of determining a reference value established on the basis of the differential waveform within a predetermined search time range;

a step of determining a first specific point and a second specific point with reference to a degree of separation from the reference value within the predetermined search time range;

a step of specifying an average value point having a position between the first specific point and the second specific point on a time axis, and having a differential value that is an average of differential values of the first specific point and the second specific point; and a step of determining a time point of the average value point as the interface arrival time point.

7. The analytical method of claim 6, wherein the step of determining the first specific point and the second specific point includes:

a step of taking a point, which is located furthest from the reference value at a negative direction side along a differential value axis within the predetermined search time range, as a first feature point;

a step of taking a point, which is located furthest from the first feature point along the differential value axis at a negative direction side along the time axis within the predetermined search time range, as a second feature point;

a step of taking a point, which is located furthest from the first feature point along the differential value axis at a positive direction side along the time axis within the predetermined search time range, as a third feature point;

a step of taking a point, which is located furthest from the third feature point at a positive direction side along the time axis in the predetermined search time range, as a fourth feature point; and a step of selecting two points among the first to fourth feature points that are located furthest from each other along the differential value axis as the first specific point and the second specific point.

8. The analytical method of claim 7, wherein a disposable analysis chip provided with the micro flow path is used.

9. An analytical system for analyzing a component contained in a sample solution introduced to a micro flow path filled with a migration liquid by using capillary electrophoresis, the analytical system comprising:

a measurement section configured to measure an optically measured value on a predetermined measurement position of the micro flow path; and a control section configured to
determine an interface arrival time point when an interface between the sample solution and the migration liquid reaches the predetermined measurement position and a component arrival time point when the component reaches the predetermined measurement position based on the optically measured value, and to identify the component based on an elapsed time from the interface arrival time point to the component arrival time point.

10. The analytical system of claim 9, wherein the sample solution is a solution containing blood as the sample, and the component is hemoglobin.

11. The analytical system of claim 9, wherein the interface arrival time point is determined based on the optically measured value.

12. The analytical system of claim 11, wherein:
the optically measured value is an absorbance;
the control section is configured to form a waveform related to the absorbance corresponding to the elapsed time after applying a voltage to the sample solution; and
the interface arrival time is determined based on the waveform.

13. The analytical system of claim 12, wherein a disposable analysis chip provided with the micro flow path is used.

14. The analytical method of claim 1, wherein the process of identifying the component is based on the elapsed time from the interface arrival time point to the component arrival time point, and an elapsed time from the interface arrival time point to a known component arrival time point.

15. The analytical system of claim 9, wherein the control section is configured to identify the component based on the elapsed time from the interface arrival time point to the component arrival time point, and an elapsed time from the interface arrival time point to a known component arrival time point.

* * * * *